United States Patent [19]

Jansman et al.

[11] Patent Number: 5,152,855
[45] Date of Patent: Oct. 6, 1992

[54] METHOD AND DEVICE FOR MUTUAL CONNECTION OF TUBES

[75] Inventors: G. Jansman, Roden; H. W. Wegereef, Peize, both of Netherlands

[73] Assignee: Cordis Europa N.V., Roden, Netherlands

[21] Appl. No.: 546,013

[22] Filed: Jun. 28, 1990

[30] Foreign Application Priority Data

Jun. 29, 1989 [NL] Netherlands .......... 8901654

[51] Int. Cl.⁵ .............................. B29C 65/06
[52] U.S. Cl. ................ 156/73.5; 156/580.2; 264/68
[58] Field of Search ............ 156/73.5, 580.2; 264/68; 604/280; 228/2, 112

[56] References Cited

U.S. PATENT DOCUMENTS

| | | | |
|---|---|---|---|
| 2,963,394 | 12/1960 | Wilkinson | 156/304.2 X |
| 3,002,871 | 10/1961 | Tramm et al. | 156/73.5 X |
| 3,890,976 | 6/1975 | Bazell et al. | 604/280 X |
| 3,917,497 | 11/1975 | Stickler | 156/73.5 |
| 3,934,780 | 1/1976 | Flax | 228/2 |
| 4,385,635 | 5/1983 | Ruiz | 128/658 |
| 4,440,338 | 4/1984 | Stevenson | 228/2 |
| 4,495,134 | 1/1985 | Ouchi et al. | 264/516 |
| 4,523,968 | 6/1985 | McCool | 156/73.5 |
| 4,551,292 | 11/1985 | Fletcher et al. | 264/139 |
| 4,596,563 | 6/1986 | Pande | 604/264 |
| 4,753,765 | 6/1988 | Pande | 264/149 |

FOREIGN PATENT DOCUMENTS

7320641  1/1974  France.
2016274  9/1979  United Kingdom.

Primary Examiner—David A. Simmons
Assistant Examiner—J. Sells
Attorney, Agent, or Firm—Lockwood, Alex, Fitzgibbon & Cummings

[57] ABSTRACT

A spinwelding procedure is provided for joining thermoplastic tubular members together at their respective axial ends. Axial end portions of very thin tubes are circumferentially supported both internally and externally, and one of the tubes is then rotated with respect to the other until adequate friction develops to melt the thermoplastic materials, after which they cool to heat bond together.

6 Claims, 3 Drawing Sheets

METHOD AND DEVICE FOR MUTUAL CONNECTION OF TUBES

DESCRIPTION

Background and Description of the Invention

The invention generally relates to the mutual connection of two tube-like elements of thermoplastic material. More particularly, the mutual connection is carried out by what may be described as a spinwelding technique which is suitable for joining tube-like elements which are of extremely small diameter and are very thin-walled.

What is understood by a tube or tube-like element in this context is an element which, at least at the end where a connection to another tube must take place, is tube-like, that is it has an annular cross section.

A usual method of joining tube-like elements is to attempt to glue the respective end faces of the tubes against one another. The smaller the diameter of the tubes being connected together becomes, the more difficult it is to form a good and secure connection wherein the tubes are perfectly coaxial with one another. Automating the forming of adhesive joints is also very difficult.

It is a general object of the present invention to provide a spinwelding method with which tubes can be connected to one another precisely and rapidly, which method is suitable for automation, as well as to provide devices such as catheters which are produced by this spinwelding method.

The method according to the invention includes the forming or providing of an axial end face on each tube, positioning the tubes with the axial end faces against one another in order that the respective central channels of the tubes are in axial communication and alignment with each other. A close-fitting mandrel or core is arranged within the central channels, and a close-fitting sleeve is arranged around the tubes. Then, at least one of the tubes is rotated relative to the other, and at the same time at least one of the tubes is urged in an axial direction toward the other tube in order to heat the end faces through frictional heat to a softening temperature of the thermoplastic material or materials out of which the tubes are made. During this procedure, the portions of the tubes which are close to the end faces the tubes are held enclosed or encased in each radial direction between the core and the sleeve. After the rotation is completed, the tubes are allowed to cool at least slightly, and the core and the sleeve are removed, whereby the tubes are butt welded to one another.

Rotational butt welding per se is known in the art, particularly in the art of welding metals. Rotational butt welding is also employed for stiff plastic parts. In the usual rotational butt welding method, a portion of the softened material is pressed radially outwardly whereby a frayed collar is formed at the position of the weld. The customary method is therefore unsuitable for connecting hollow parts, particularly those which are tubular or tube-like, since having a frayed collar formed in the central channel will at least obstruct or even block the passageways of the tubular parts.

By virtue of this enclosing of the tubes close to the end faces according to the invention by means of a core arranged in the central channel and a sleeve arranged around the outside of the tubes, any possible radial flow of softened material is prevented. Otherwise, it is possible for an undesired collar to be formed by an unchecked flow of molten or softened polymer material. It is, therefore, usually unnecessary to proceed with finishing of the weld.

Tubes of soft plastic can also be joined to one another by practicing the method according to the invention. The sleeve and the core stabilize so that during the process they remain directed accurately relative to one another and relative to their common axis.

In the method according to the invention, the core remains accurately centered throughout the procedure because it is supported at portions of the tube which do not soften. While the thermoplastic material of the two tubes can flow together at the location of their respective end faces, the central channel common to the tubes being joined nevertheless remains accurately centered.

The method according to the invention is particularly suitable for use in the manufacture of angiographic catheters. These typically comprise a tube-like body and a tube-like end part or tip portion that is more flexible than the body. There is a noticeable trend in the development of angiographic catheters toward smaller diameters and smaller wall thicknesses. Wall thicknesses of only several tenths of a millimeter are now being achieved. With the method according to the invention such thin elements can also be mutually connected in a reliable manner. Through the inherent centering of the parts by the core and the sleeve, a high-grade continuity of the section is also obtained at the position of the weld in the case of very small wall thicknesses.

The invention can also be applied in a very favorable manner in the manufacture of angiographic catheters of the type wherein the body includes an embedded reinforcing layer of thin braided wires. It is of course not acceptable that wires of these types of reinforcing layers protrude out of the outer periphery of the catheter or into the central channel thereof. Because of the complete enclosure of the parts between the sleeve and the core, there is no flow in any radial direction, so that the wires of such a reinforcing layer are not subjected to any radial forces at the location of the end face of the body and thus remain lying precisely at their original location and diameter within the thickness of the wall.

Although a mandrel or core could be used that is divided at the location of the abutting end faces, it is preferred that the mandrel or core extends continuously over a distance at either side of the abutting end faces. The centering of the core is thereby better ensured. Also ensured is that the central channel obtains a smooth wall at the location of the weld formed according to the invention.

In connection with the manufacture of angiographic catheters, the material out of which the tubular body member is made is usually formed continuously onto a long, continuous mandrel or core, and the metal core or mandrel can remain within the tubular member in order to fully support the body and maintain its central channel during handling. This metal core wire is removed at a later stage of manufacture, leaving the central channel in the catheter. A preferred embodiment of the method according to the invention in this respect dispenses with a separate step of arranging the core wire. In this arrangement, a portion of the tubular body component is removed from its underlying mandrel or core in order to expose a portion of the mandrel or core, after which the end part or tip portion to be joined to the body is slid thereonto. Thus, the mandrel or core of the tubular body component is used as the core support utilized during the rotational butt welding procedure.

In accordance with the preferred method, the tubes are constrained toward one another with a constant force. At a fixed rotation speed the quality of the weld can then be simply determined by the time duration. In this way, the rotational butt welding method can be automated effectively.

The invention also relates to and provides an apparatus or device for rotational butt welding of two tubes. This device includes a frame, first holding means connected to the frame for fixedly holding an end of the first tube directed along an axis, second holding means connected to the frame for fixedly holding an end of the second tube directed along the axis, a sleeve disposed co-axially with the axis between the first and second holding means, and a core to be received in a central channel of the first tube and second tube. At least one of the first and second holding means is connected to the frame for rotation along the axis and can be rotated by rotation drive means. At least one of the first and second holding means is connected to the frame for movement toward the other and can be urged toward this other one by loading means for applying a generally axially directed force. By separating the rotation function from the pressure applying function, a comparatively simple construction can be realized, such as by having the first holding means rotatably connected to the frame and the second holding means slidably connected to the frame for facilitating movement of the non-rotating second holding means toward the first holding means.

DESCRIPTION OF THE DRAWINGS

The invention will be further understood and described in the following description with reference to the attached drawings, wherein.

DETAILED DESCRIPTON OF THE INVENTION

Figure 1:
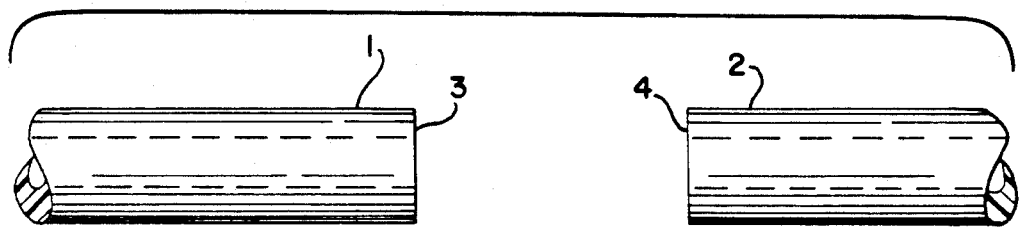
FIGS. 1 through 3 are somewhat schematic illustrations of the basic steps of the method according to the invention.

The method according to the invention is intended for accomplishing the mutual connection in lengthwise direction of a first tube 1 and a second tube 2, cutaway portions of which are shown in FIG. 1. The tubes 1 and 2 are made of the same or different thermoplastic materials such as a polyolefin, a polyamide, a polyester, a polyurethane or copolymers and the like. Since the tubes 1 and 2 do not need to have any inherent stiffness for application of the method thereto, the thermoplastic of either or both tubes may be made of a soft, flexible plastic as needed for the use intended for the catheter or other device being made.

For application of the method, axial end faces 3 and 4 are formed on each respective tube 1 and 2. These axial end faces 3 and 4 are usually already formed during cutting of the tubes 1 and 2 from a greater length of base material therefor.

Figure 2:
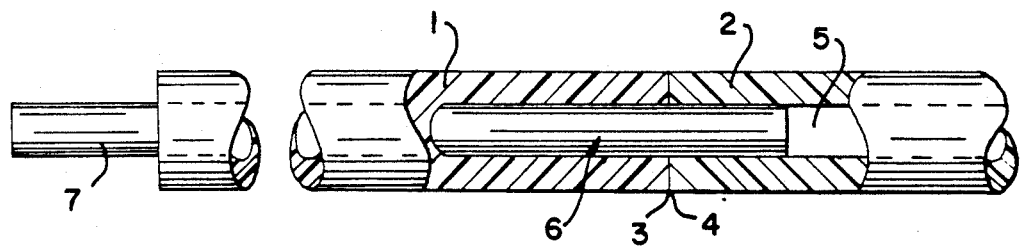
Figure 3:
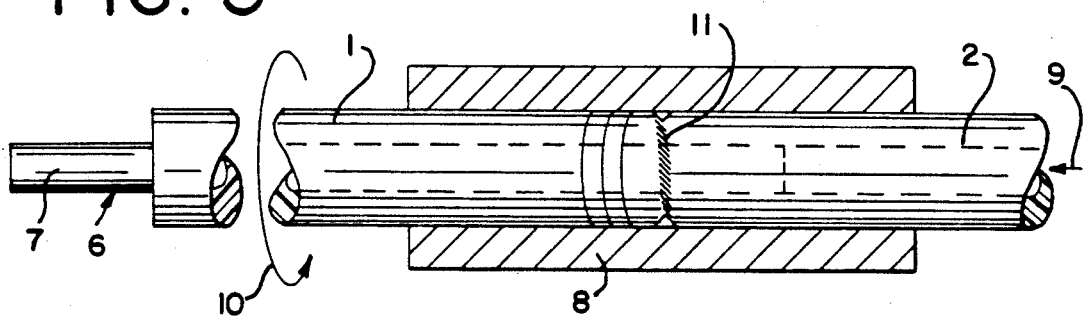

As shown in FIG. 2, in a subsequent step of the method according to the invention, the tubes 1 and 2 are positioned end-to-end with their end faces 3 and 4 abutting one another. Inserted into the respective communicating central channels 5 of the tube portions 1 and 2 is a close-fitting core or mandrel 6. This core 6 is for example a metal wire or rod with an outer diameter corresponding to the inner diameter of the central channel 5. As FIG. 2 shows, the core 6 is arranged according to this embodiment of the method such that it extends entirely through the tube 1 and over a determined distance into the tube 2. An end 7 of the core 6 protrudes beyond the tube 1 so that the core 6 can be grasped after welding has been completed to remove it from the tubes which are mutually connected according to the invention. At the location of the abutting end faces 3 and 4, a sleeve 8 is moreover arranged around the tubes 1 and 2 as indicated in FIG. 3. The sleeve 8 has an internal channel which is a cylindrical surface having a diameter corresponding to the outer diameter of the tubes 1 and 2 to be connected together.

The internal diameter of the sleeve 8 and the outer diameter of the core 6 furthermore are selected such that the tubes 1 and 2 can rotate without considerable friction relative to the sleeve 8 and the core 6. When arranging the core 6 and the sleeve 8, a lubricant optionally can be used which facilitates the relative turning of the components. This lubricant may be water or a suitable wax or the like.

With the tubes 1 and 2 enclosed in the radial direction between the core 6 and the sleeve 8 at the location of the two abutting end faces 3 and 4, the tube 1 is rotated relative to tube 2, as designated with the arrow 10, while the two tubes 1 and 2 are constrained or manipulated so they are relatively urged in the axial direction toward one another, as designated by the arrow 9 in FIG. 3. Because of the relative rotation of the tubes, the end faces 3 and 4 slide against one another. Because the faces 3 and 4 are pressed against one another, frictional forces develop by the relative rotation of the faces 3 and 4. This friction causes the generation of heat whereby the temperature of the material of the tubes 1 and 2 increases at the location of the end faces 3 and 4. The relative rotation and axial pressing is maintained until the temperature exceeds the softening temperature of the material of which the tubes 1 and 2 are made. In this situation the material of the tubes 1 and 2 fuses, whereby a weld 11 is formed. By now stopping the rotation and allowing the weld 11 to cool, a strong joint is formed between the tubes 1 and 2. During cooling the axial force illustrated by arrow 9 preferably is maintained.

Due to the encapsulation of the end portions of the tubes 1 and 2 between the core 6 and the sleeve 8, no tube material can flow away in any radial direction. The tubes 1 and 2 welded together in this way therefore do not display any bulges or interruptions at the location of the weld 11.

Because the core 6 is supported centered in the central channel on either side at a distance from the weld 11 and because the tubes 1 and 2 are supported centered in the sleeve 8, the core 6 likewise remains accurately centered in the sleeve 8 at the location of the weld 11. The central channel thus also remains accurately centered in the tubes 1 and 2 at the position of the weld 11.

In the embodiment of the method according to the invention shown in FIGS. 1 through 3, the core 6 will rotate with the tube 1. The portion of the core 6 extending into the central channel 5 of tube 2 therefore rotates in that channel. Through a correct dimensioning of the core 6 and optional use of lubricants, as noted above, the friction in the central channel 5 is minimized so that any frictional heat developed between the tubes 1 and 2 and the core 6 is insufficient to heat the material of the tube 2 to the softening temperature. The same applies with respect to the rotation of one or both tubes 1 and 2 in the sleeve 8.

The axial pressing force can be selected in an appropriate manner such that the frictional force at the location of the contact faces 3 and 4 remains below a value where by the tubes 1 and 2 could twist excessively. A smaller axial force means only that less heat is generated per revolution, so that that rotation must be continued for a longer time to heat the material of the tubes 1 and 2 to the softening temperature.

The parameters of pressing force, rotation speed and duration of the rotation depend on the material of the tubes 1 and 2 and can be simply determined by experiment. For example, a typical range of rotation speeds is between about 150 to about 500 revolutions per second, with a typical time of rotation being between about 0.5 and about 3 seconds under a typical compression force of between about 100 to about 500 grams. Typical catheter materials include polyolefins, polyurethanes, polyamides and other thermoplastic polymers. This invention is suitable for preparing catheters having sizing of between about French 2 to about French 8.

Figure 4:
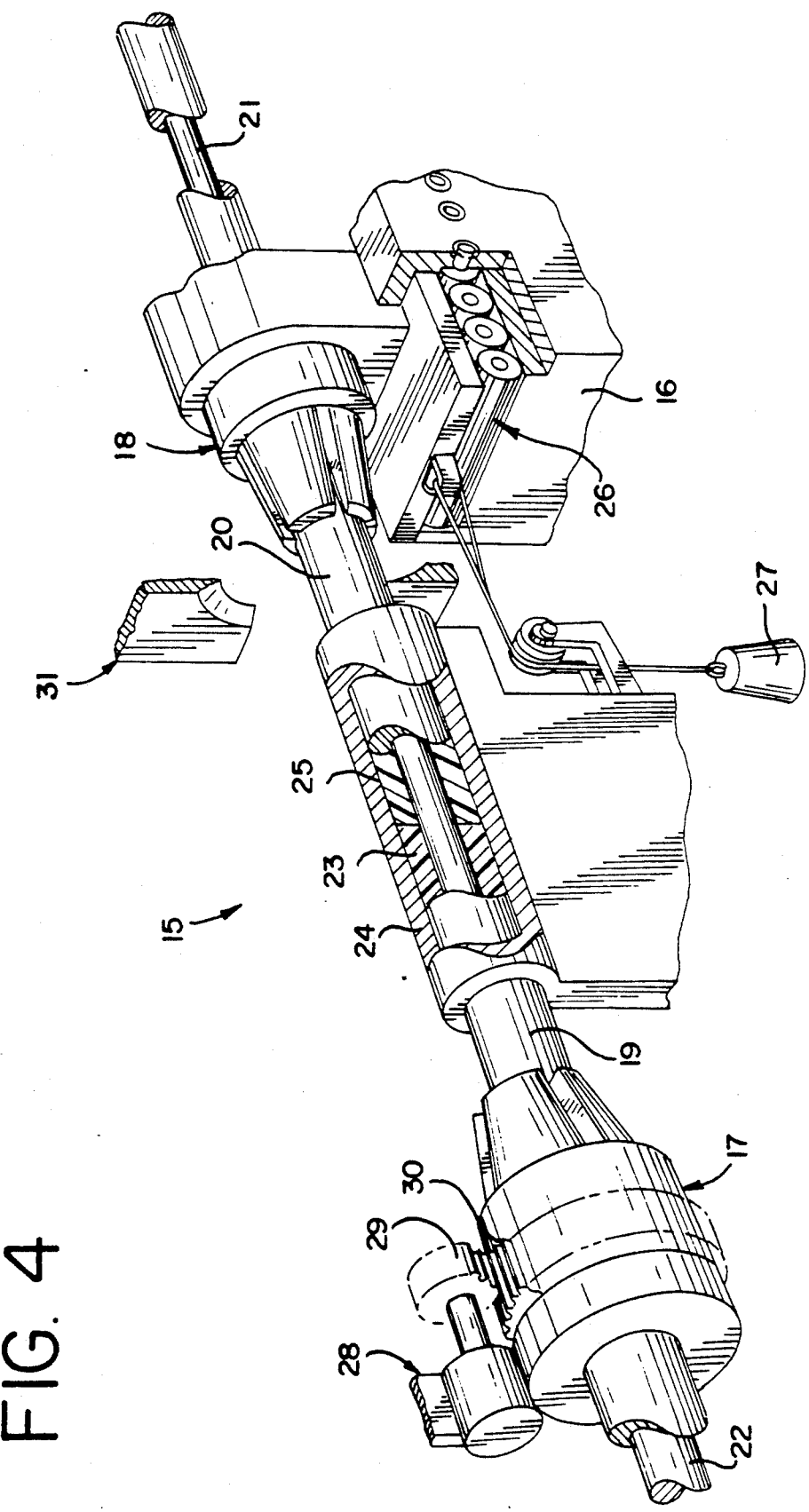
FIG. 4 is a partly broken away and somewhat schematic perspective view of an apparatus according to a preferred embodiment of the invention.
Figure 5:
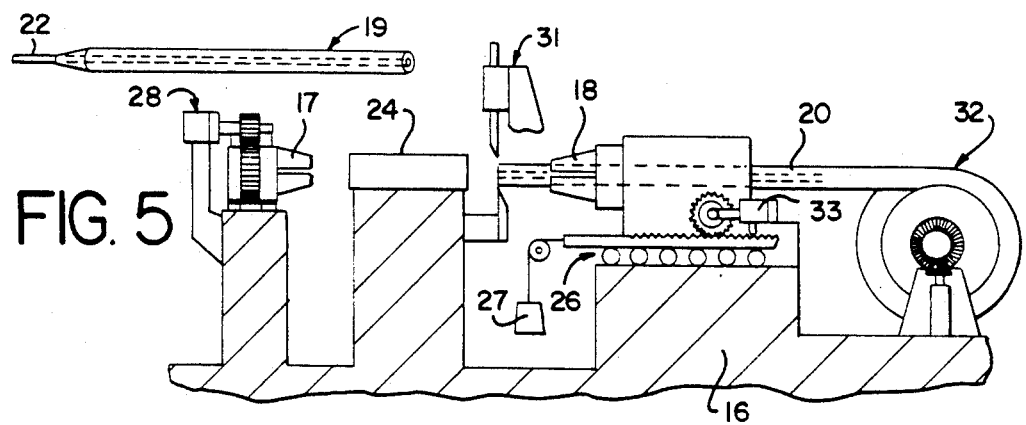
FIGS. 5 through 8 are generally schematic elevational views showing the different stages carried out during the operation of the device of FIG. 4.

The device 15 according to the invention shown schematically in FIG. 4 is intended for use in the manufacture of angiographic catheters. This device 15 comprises a frame 16 to which are connected first holding means in the form of a chuck 17 or the like for fixedly holding a catheter end part 19 and second holding means in the form of a chuck 18 or the like for fixedly holding a catheter basic body part or component 20. The chucks 17 and 18 are self-centering so that they can hold the catheter parts 19 and 20, respectively, in place directed along an axis. Arranged between the chucks 17 and 18 is a sleeve 24 which is fixedly connected to the frame 16 and co-axial to said axis.

Typically, the catheter body 20 is formed on a metal core wire or mandrel 21. For connecting the end part 19 to the body component 20, the core wire 21 preferably is not removed as yet, but it is used as a core for connection thereto of the catheter end part using the method according to the invention.

The various phases in the operation of the device 15 are depicted schematically in FIGS. 5 through 8. In this illustrated embodiment, the material for forming the basic body 20 of the catheter is produced in a continuous length using a generally known method and device for extruding the material over the coil or mandrel which is then wound onto a reel 32. As noted, this material is formed on the core wire or mandrel 21, and the base material which is wound onto the reel 32 still contains this metal core wire.

The illustrated chuck 18 is mounted on frame 16 for movement in the direction of the axis by means of a roller guiding assembly 26. The chuck 18 can be constrained with a constant force to the left as seen in the Figures. In the drawings, this constant force is generated using a weight 27.

In order to be able to move the chuck 18 to the right and counter to the force exerted by the weight 27, a retracting device 33 is arranged as shown schematically. The illustrated arrangement uses a pinion onto a rack which is connected fixedly to the head 18.

The catheter basic body component 20 that is still connected to the stock on the reel 32 is taken up in the chuck 18, and a cutting device 31 can form an axial end face on the body component 20. The catheter end part component 19 to be connected to the basic body component 20 is for example likewise cut off from a greater length, and a support wire 22 is inserted into a central channel thereof. The support wire 22 is arranged in the central end face up to a distance from the end face for connection.

Figure 6:
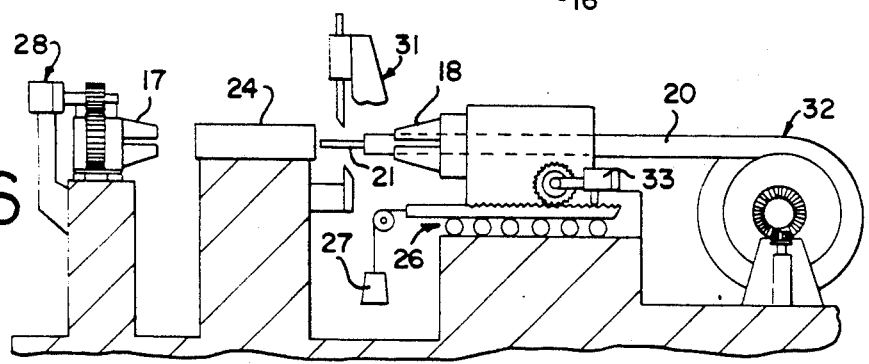

As shown in FIG. 6, an end portion preferably is removed from the basic body component 20 while it is clamped in the chuck 18. This removal is accomplished so that the core wire 21 protrudes beyond the end face of the basic body component 20.

Figure 7:
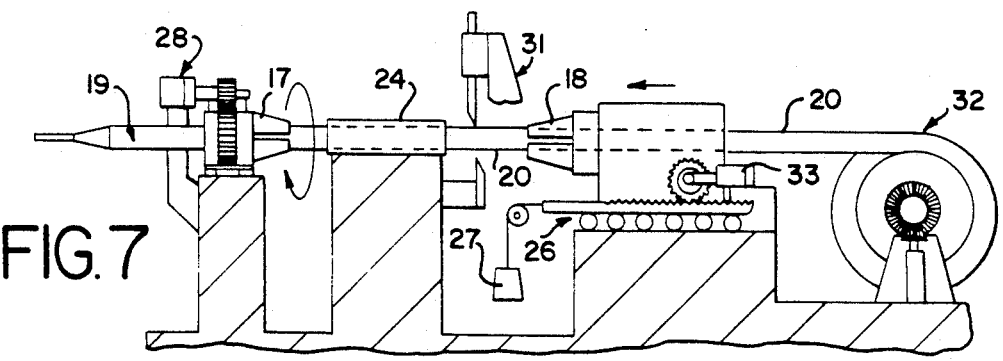
Figure 8:
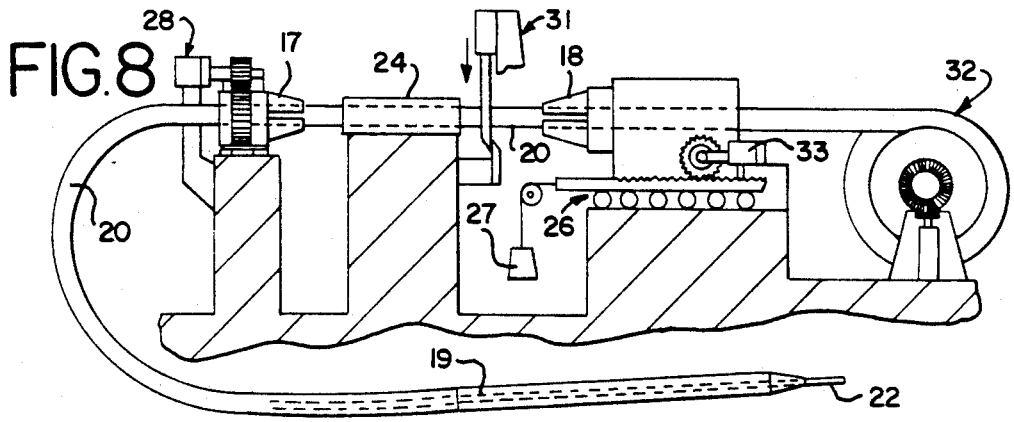

As shown in FIG. 7, the body component 20 is then inserted into the sleeve 24, and the catheter end part component 19 is pushed, together with its central channel 23 onto the protruding portion of the core wire 21 and likewise received within the sleeve. The catheter end part component 19 is clamped fixedly in the chuck 17, and the basic body component 20 in this situation likewise is clamped fixedly in the chuck 18. To form the weld, the chuck 17 is then set into rotation using the rotating device 28. The preferred rotating device 28, perhaps best shown in FIG. 4, is a motor-driven pinion 29 that is in engagement with a toothing on the periphery of the chuck 17. At the same time, the weight 27 is active, whereby the basic body component 20 is constrained in the direction to the left as illustrated in the drawings. At the position of the contact surface between the catheter end component 19 and catheter basic body component 20, heat of rotational friction is developed, whereby the weld connection between the basic body component 20 and the end part component 19 as described with reference to FIGS. 1 through 3 is effected.

After a period of time adequate to achieve desired welding for the particular components, the rotating means 28 are switched off while the chuck 18 still remains urged to the left under the influence of the weight 27. The softened or melted material of the end part and body components which has flown together cools off, and this melted thermoplastic material once again hardens. Due to the continuation of the pressing force, the occurrence of cavities, for instance as a result of shrinkage, is prevented. It is thus of importance herein that the core wire 21 and the support wire 22, when provided, be spaced apart and do not abut one another in order not to obstruct the feed in the direction of the pressing force.

After the weld has cooled sufficiently, the chucks 17 and 18 are released, and a length of base or body material is pushed through such as is required for manufacturing the catheter. The base or body material is subsequently cut off using the cutting device 31. The assembly of catheter basic body component 20 and catheter end part component 19 is further finished thereafter, which includes among other things the removal of core and support wires 21 and 22. The next assembly is then formed by a subsequent weld operation which begins with the step as designated in FIG. 5.

FIG. 4 also shows that the basic body component 20 can be of a type comprising a reinforcing layer 25 of woven metal wire. As mentioned herein, no material flow occurs in a direction transverse to the axis during the welding operation, with the result that the reinforcing layer 25 maintains its radial shape and location, and no wires of the reinforcing layer, when present, protrude inwardly or outwardly after the welding operation has been accomplished.

The support wire 22 has the purpose of enabling the catheter end part component 19 to be clamped stably in the chuck 17 without the central channel 23 thereby being pressed shut. The support wire 22 may have a slightly smaller diameter than the central channel 23 in order to be able to push it in easily. The core wire 21 only needs to be inserted into the catheter end part component 19 over a short distance so that a smooth transition results from the central channel of the end part component 19 to the central channel of the basic body component 20. The invention can further be modified depending on the tube parts or components to be connected together. One or both tube parts can thus be heated beforehand at the position of the contact surfaces or can be additionally heated during welding. In the case of types of material that are difficult to connect to each other directly, an intermediate tube portion can be used which connects readily to each of the materials. This intermediate tube portion can be very short and can be arranged in one operation between the two tube parts to be connected.

It will be understood that the embodiments of the present invention which have been described are illustrative of some of the applications of the principles of the present invention. Numerous modifications may be made by those skilled in the art without departing from the true spirit and scope of the invention.

We claim:

1. A method for the mutual connection in a longitudinal direction of a first tube and a second tube of thermoplastic material, comprising the steps of:

providing a first tube and a second tube, each said tube having a central channel therethrough and each said tube having an axial end face thereon, said first tube and second tube being for forming a body component and a tip component of an angiographic catheter;

providing a supply of said first tube with a close-fitting core within the central channel thereof, removing a portion of the first tube from the core to form a protruding portion of the core;

pushing the second tube onto the protruding portion of the core so that the core forms a core mandrel within both of the central channels during rotational butt welding of the tip component to the body component, and positioning the tubes with their respective axial end faces against one another wherein the respective central channels thereof are in axial alignment, including positioning a close-fitting sleeve around the tubes;

rotating at least one of the tubes relative to the other and at the same time urging at least one of the tubes in the axial direction such that the tubes are urged toward one another in order to heat the end faces through frictional heat to a softening temperature of the thermoplastic tubes;

said positioning step holds the end faces of the tubes enclosed in radial direction between the core mandrel and the sleeve during said rotating and urging steps;

completing said rotating step and allowing the tubes to cool at least slightly; and removing the core mandrel and the sleeve from the tubes, whereby the tubes are butt welded to one another.

2. The method as claimed in claim 1, wherein the body component of the providing step includes providing a tube of thermoplastic material and having a reinforcing layer of thin, braided wire embedded therewithin.

3. The method as claimed in claim 1, wherein said positioning step includes extending the core continuously over a distance at either side of the abutting end faces of the tubes.

4. The method as claimed in claim 1, wherein said providing step includes providing the body component with a metal core as the core within the central channel thereof, said removing step removes a portion of the body component from the metal core to form the protruding portion of the metal core, and said pushing step pushes the catheter tip component onto the protruding portion of the metal core.

5. The method as claimed in claim 1, wherein the urging step applies a substantially constant force.

6. A catheter manufactured according to the method of claim 1, wherein the first tube is a catheter body and the second tube is a catheter tip.

* * * * *